US011940376B2

(12) United States Patent
Jin et al.

(10) Patent No.: US 11,940,376 B2
(45) Date of Patent: Mar. 26, 2024

(54) SYSTEM AND METHOD FOR DETECTING CONCENTRATION OF FREE SiO2 IN COAL DUST

(71) Applicant: Anhui University of Science and Technology, Huainan (CN)

(72) Inventors: Huawei Jin, Huainan (CN); Fangzheng Yan, Huainan (CN); Lei Fang, Huainan (CN)

(73) Assignee: Anhui University of Science and Technology, Huainan (CN)

( * ) Notice: Subject to any disclaimer, the term of this patent is extended or adjusted under 35 U.S.C. 154(b) by 0 days.

(21) Appl. No.: 18/147,236

(22) Filed: Dec. 28, 2022

(65) Prior Publication Data

US 2023/0314308 A1 Oct. 5, 2023

Related U.S. Application Data

(63) Continuation of application No. PCT/CN2022/087378, filed on Apr. 18, 2022.

(30) Foreign Application Priority Data

Mar. 29, 2022 (CN) .......................... 202210322992.4

(51) Int. Cl.
*G01N 21/17* (2006.01)
*G01N 1/20* (2006.01)
(Continued)

(52) U.S. Cl.
CPC ........... *G01N 21/1702* (2013.01); *G01N 1/24* (2013.01); *G01N 33/0027* (2013.01); *G01N 2021/1704* (2013.01); *G01N 2201/06113* (2013.01)

(58) Field of Classification Search
CPC ........ G01N 33/0027; G01N 1/24; G01N 1/20; G01N 1/2294; G01N 21/1702; G01N 2001/227; G01N 2021/1704
(Continued)

(56) References Cited

U.S. PATENT DOCUMENTS 11,662,301 B1 * 5/2023 Jin ..................... G01N 21/1702
436/173
2003/0160174 A1 8/2003 Grant et al.

FOREIGN PATENT DOCUMENTS

CN 202404020 U 8/2012
CN 203881653 U 10/2014
(Continued)

OTHER PUBLICATIONS

Klinger, N. et al., Journal of the American Ceramic Society 1966, 49, 369-375. (Year: 1966).*
(Continued)

*Primary Examiner* — Arlen Soderquist
(74) *Attorney, Agent, or Firm* — Westbridge IP LLC

(57) ABSTRACT

A system for detecting a concentration of free $SiO_2$ in coal dust includes a first sampling tube and a second sampling tube for sampling the coal dust, a three-way control valve communicated with the first sampling tube and the second sampling tube respectively, a photoacoustic spectrometry detection device communicated with the three-way control valve through a connecting pipeline, and a $SiO_2$ reaction tube for reacting $SiO_2$ in the coal dust; and the $SiO_2$ reaction tube is disposed on the second sampling tube. In the present disclosure, a coal dust sampling line is convenient to change by disposing the three-way control valve, and the first sampling tube and the second sampling tube are respectively communicated with the photoacoustic spectrometry detec-
(Continued)

tion device, so as to perform a differential accurate detection of the reacted CO content, and to obtain the $SiO_2$ content.

5 Claims, 1 Drawing Sheet

(51) Int. Cl.
*G01N 1/22* (2006.01)
*G01N 1/24* (2006.01)
*G01N 33/00* (2006.01)

(58) Field of Classification Search
USPC .......................................................... 436/72
See application file for complete search history.

(56) References Cited

FOREIGN PATENT DOCUMENTS

| | | |
|---|---|---|
| CN | 105067493 A | 11/2015 |
| CN | 106596198 A | 4/2017 |
| CN | 108061722 A | 5/2018 |
| CN | 108387479 A | 8/2018 |
| CN | 108776091 A | 11/2018 |
| CN | 210322955 U | 4/2020 |
| CN | 111175168 A | 5/2020 |
| CN | 210571936 U | 5/2020 |
| CN | 111398082 A | 7/2020 |
| CN | 211785111 U | 10/2020 |
| CN | 212321419 U | 1/2021 |
| CN | 113358535 A | 9/2021 |
| RU | 2383493 C1 | 3/2010 |

OTHER PUBLICATIONS

Paull, J. M. et al., Journal of the South African Institute of Mining and Metallurgy 1978, 79, 35-41 (Year: 1978).*
Ryabchikova, I. V. et al., Steel in Translation 2014, 44, 368-373 (Year: 2014).*
Pedersen, R. T., Thesis 2019, 56 pages. (Year: 2019).*
Wei, S., Dissertation 2020, 116 pages. (Year: 2020).*
Taylor, S., Thesis 2021, 77 pages. (Year: 2021).*
International Search Report issued in corresponding PCT Application No. PCT/CN2022/087378, dated Dec. 27, 2022.
First Office Action issued in counterpart Chinese Patent Application No. 202210322992.4, dated Sep. 8, 2022.

* cited by examiner

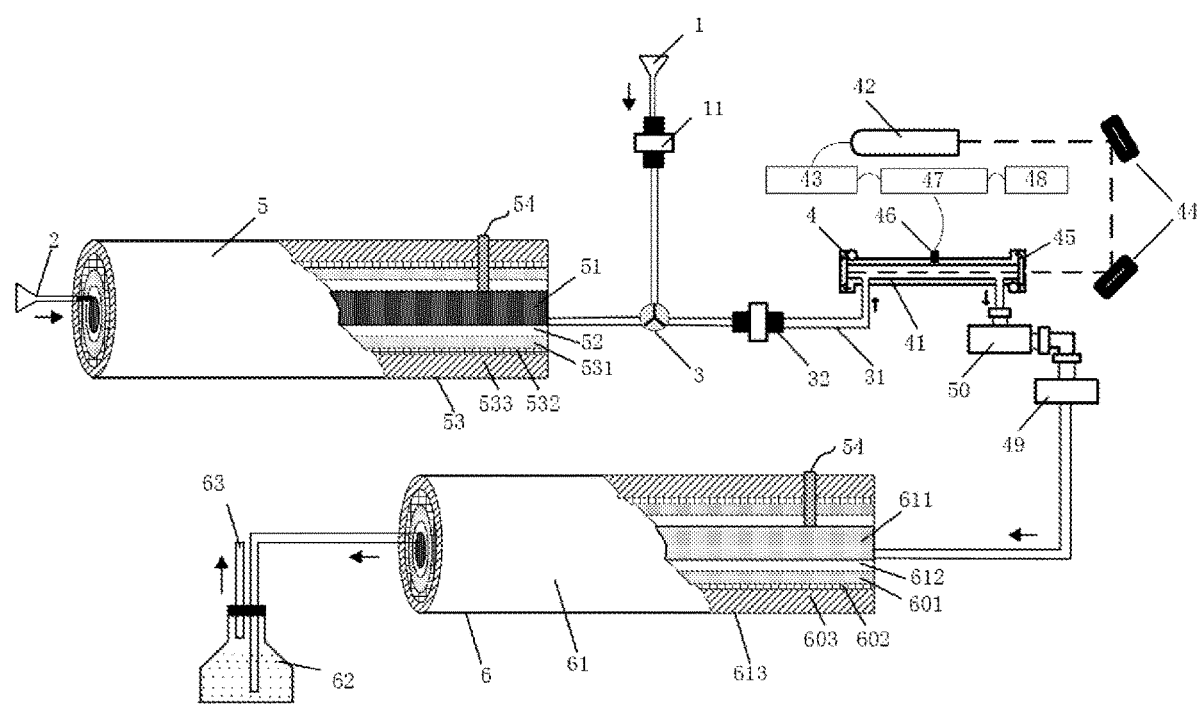

SYSTEM AND METHOD FOR DETECTING CONCENTRATION OF FREE SiO2 IN COAL DUST

CROSS-REFERENCE TO RELATED APPLICATION

This application is a continuation of International Application No. PCT/CN2022/087378, filed on Apr. 18, 2022, which claims priority to Chinese Patent Application No. 202210322992.4, filed on Mar. 29, 2022, the entire contents of which are incorporated herein by reference.

TECHNICAL FIELD

The present disclosure relates to the detection field for coal dust, in particular to a system and a method for detecting a concentration of free $SiO_2$ in coal dust.

BACKGROUND

Respirable dust is a main factor leading to pneumoconiosis, however the pneumoconiosis is the most serious occupational disease in some countries. Safety Regulations in Coal Mine stipulates that a coal mine enterprise must monitor the underground productive dust. When the free $SiO_2$ content in the dust is less than 10%, the respirable dust under the permissible concentration-time weighted average should be less than 2.5 $mg/m^3$, and the total dust should be less than 4 $mg/m^3$, etc. Thus, the free $SiO_2$ content in the dust is the important basis for judging whether the dust exceeds the standard, Safety Regulations in Coal Mine stipulates that the free $SiO_2$ content in the dust must be measured every half year. $SiO_2$ floats in the coal dust air in a free and gaseous form, with less content. Most of the existing detection technologies are offline sampling, the online detection cannot be achieved, so there are great defects in real-time and accuracy.

SUMMARY

In order to solve the defects in the prior art, the present disclosure aims at providing a system and a method for detecting a concentration of free $SiO_2$ in coal dust. Based on a characteristic that $SiO_2$ reacts with C at a high temperature to generate solid Si and gaseous CO, and $SiO_2$ is quantificationally acquired by detecting a CO content and used as a basis for judging a free $SiO_2$ content in the coal dust. Based on another characteristic that CO reacts with CuO at a high temperature to generate solid Cu and gaseous $CO_2$ and $CO_2$ reacts with liquid NaOH to generate liquid $NaCO_3$ and $H_2O$, a tail gas treatment is carried out. Based on a photoacoustic effect, a photoacoustic spectrometry system detects the CO content accurately in a specific infrared band; and the system and the method solve the problem that the free $SiO_2$ in the coal dust cannot be detected in real time, with a high precision and a low cost.

In order to solve the problem technical problem, the present disclosure adopts the technical solution below: a system for detecting a concentration of free $SiO_2$ in coal dust, including a first sampling tube and a second sampling tube for sampling the coal dust, a three-way control valve communicated with the first sampling tube and the second sampling tube respectively, a photoacoustic spectrometry detection device communicated with the three-way control valve through a connecting pipeline, and a $SiO_2$ reaction tube for reacting $SiO_2$ in the coal dust; and the $SiO_2$ reaction tube is disposed on the second sampling tube.

Further, the $SiO_2$ reaction tube includes a carbon tube and an air inlet heating tape from inside to outside, the carbon tube is heated through the air inlet heating tape, the $SiO_2$ in the coal dust delivered by the second sampling tube reacts with the heated carbon tube, and reacted gas is delivered into the photoacoustic spectrometry detection device through the three-way control valve.

Further, a first insulation layer is disposed outside the air inlet heating tape, and the first insulation layer includes an air inlet high temperature resistant quartz felt, an air inlet high temperature resistant quartz fiber and an air inlet high temperature resistant insulation cotton from inside to outside.

Further, the photoacoustic spectrometry detection device includes a photoacoustic cavity communicated with the connecting pipeline, a laser device, a signal modulator, a reflector, quartz windows disposed at two ends of the photoacoustic cavity, a rheomicrophone disposed at a middle of the photoacoustic cavity, a lock-in amplifier for collecting and amplifying a photoacoustic signal generated by the rheomicrophone and a detection software; and the laser device outputs laser through the signal modulator, and after the reflector reflects the laser, the laser enters the photoacoustic cavity through the quartz windows.

Further, the photoacoustic spectrometry detection device further includes a sampling pump for extracting gas and a flowmeter disposed on the sampling pump.

Further, the system further includes a tail gas treatment device, which includes a tail gas conversion tube communicated with an air outlet of the sampling pump and a NaOH liquid bottle communicated with the tail gas conversion tube, and the NaOH liquid bottle is provided with an air outlet tube for discharging the processed tail gas.

Further, the tail gas conversion tube includes an oxidized copper tube and an air outlet heating tape for heating the oxidized copper tube from inside to outside.

Further, a second insulation layer is disposed outside the air outlet heating tape, and the second insulation layer includes an air outlet high temperature resistant quartz felt, an air outlet high temperature resistant quartz fiber and an air outlet high temperature resistant insulation cotton from inside to outside.

Further, temperature probes are respectively disposed on the $SiO_2$ reaction tube and the tail gas conversion tube.

Preferably, a first filtering membrane is disposed on the first sampling tube.

Preferably, a second filtering membrane is disposed on the connecting pipeline.

A method for detecting a concentration of free $SiO_2$ in coal dust adopts the above system for detecting the concentration of the free $SiO_2$ in the coal dust, and the detection steps are as follows:

Step 1: regulating a three-way control valve to a background sampling gas circuit, namely, a gas circuit of a first sampling tube, and at this time, an object to be measured entering a photoacoustic spectrometry detection device being background CO of the coal dust;

Step 2: starting a sampling pump for air exhaust, controlling coal dust entering flow through a flowmeter, the coal dust entering through the first sampling tube and entering a photoacoustic cavity through the three-way control valve;

Step 3: a laser device outputting a square wave modulation signal through a signal modulator to send out laser, a reflector reflecting the laser and then the laser entering the photoacoustic cavity through quartz windows, the laser stimulating a CO gas based on a photoacoustic effect so as to generate a sound pressure wave section and drive a rheomicrophone disposed on the photoacoustic cavity to generate a photoacoustic signal, and the photoacoustic signal being in direct proportion to the background CO content $Sco_{background}$;

Step 4: a detection lock-in amplifier modulated by the signal modulator collecting and amplifying the photoacoustic signal generated by the rheomicrophone, and displaying the background CO content $Sco_{background}$ on a detection software;

Step 5: regulating the three-way control valve to a gas circuit of a second sampling tube, the coal dust to be detected entering a $SiO_2$ reaction tube through the second sampling tube, an air inlet heating tape heating a carbon tube, arranging an air inlet high temperature resistant insulation cotton, an air inlet high temperature resistant quartz fiber and an air inlet high temperature resistant quartz felt outside the carbon tube for insulation, and temperature probes controlling a heating temperature;

Step 6: at a high temperature, a gaseous free $SiO_2$ in the coal dust reacting and generating solid Si and gaseous CO, the reacted gas entering the photoacoustic cavity through the three-way control valve, repeating the step 3 to detect the gas, at this time, obtaining the reacted total CO content $Sco_{total}$, subtracting the background CO content $Sco_{background}$ to obtain $Sco_{reaction}$ generated by the gaseous free $SiO_2$ reaction, and then obtaining the gaseous free $SiO_2$ content through conversion;

Step 7: a sampling pump delivering detected tail gas to a tail gas treatment device, the air inlet heating tape heating an oxidized copper tube, arranging the air inlet high temperature resistant insulation cotton, the air inlet high temperature resistant quartz fiber and the air inlet high temperature resistant quartz felt outside the oxidized copper tube for insulation, the temperature probes controlling the heating temperature, and at a high temperature, CuO in the oxidized copper tube reacting with CO in the tail gas to generate solid Cu and gaseous $CO_2$, and Step 8: after reaction in step 7, the tail gas with $CO_2$ entering a NaOH liquid bottle, $CO_2$ reacting with the liquid NaOH to generate liquid $NaCO_3$ and $H_2O$, which are discharged through an air outlet tube after completing the tail gas treatment.

Compared with the prior art, the present disclosure has the following beneficial effects: in the present disclosure, the coal dust sampling line is convenient to change by disposing the three-way control valve, and the first sampling tube and the second sampling tube are respectively communicated with the photoacoustic spectrometry detection device, so as to perform a differential accurate detection of the reacted CO content, and to obtain the $SiO_2$ content, which can be used as the basis for judging the free $SiO_2$ content in the dust coal. The system and the method solve the problem that the free $SiO_2$ in the coal dust cannot be detected in real time, with a high precision and a low cost, thereby laying the foundation for the real-time concentration monitoring of coal respirable dust.

BRIEF DESCRIPTION OF THE DRAWINGS

The specification drawings, which constitute a part of the present disclosure, are used to provide a further understanding of the present disclosure, and the exemplary embodiments of the present disclosure and the description thereof are used to explain the present disclosure, but do not constitute improper limitations to the present disclosure. In the drawings:

FIG. 1 is a structure schematic diagram of a system for detecting a concentration of free $SiO_2$ in coal dust in the present disclosure.

DETAILED DESCRIPTION OF THE EMBODIMENTS

The following clearly and completely describes the embodiments of the present disclosure with reference to the accompanying drawings in the embodiments of the present disclosure. Apparently, the described embodiments are some rather than all of the embodiments of the present disclosure. The embodiments in the present disclosure and features in the embodiments may be combined with each other without conflict. Based on the embodiments of the present disclosure, all the other embodiments obtained by those of ordinary skill in the art on the premise of not contributing creative effort should belong to the protection scope of the present disclosure.

It is to be noted that if directional indication, such as: upper, lower, left, right, front, rear, etc. is involved in the embodiments of the present disclosure, the directional indication is merely used to explain the relative position relation, movement and the like of various components under a certain special posture; and if the special posture is changed, the directional indication will change accordingly.

In addition, if the descriptions "first" and "second" are involved in the embodiments of the present disclosure, the descriptions "first" and "second" are merely used for description, instead of being understood as indicating or implying relative importance or impliedly indicating the quantity of the showed technical features. Thus, the features defined with "first" and "second" may expressly or impliedly one or more features. In addition, the meaning of "and/or" in the text includes three parallel schemes, take "A and/or B" for example, including A scheme, or B scheme, or the scheme meeting A and B at the same time. In addition, "a plurality of" means two or above two. Thus, the technical solutions of various embodiments may be mutually combined, but must be achieved by those of ordinary skill in the art. When the combination of the technical solution has mutual contradiction or cannot be achieved, it should believe that such combination of the technical solution does not exist and does not fall in the protection range required by the present disclosure.

As shown in FIG. 1, a system for detecting a concentration of free $SiO_2$ in coal dust provided by the present disclosure, including a first sampling tube 1 and a second sampling tube 2 for sampling the coal dust, a three-way control valve 3 communicated with the first sampling tube 1 and the second sampling tube 2 respectively, a photoacoustic spectrometry detection device 4 communicated with the three-way control valve 3 through a connecting pipeline 31, and a $SiO_2$ reaction tube 5 for reacting $SiO_2$ in the coal dust; and the $SiO_2$ reaction tube 5 is disposed on the second sampling tube 2.

In one embodiment, the $SiO_2$ reaction tube 5 includes a carbon tube 51 and an air inlet heating tape 52 from inside to outside, the carbon tube 51 is heated through the air inlet heating tape 52, the $SiO_2$ in the coal dust delivered by the second sampling tube 2 reacts with the heated carbon tube 51, and reacted gas is delivered into the photoacoustic spectrometry detection device 4 through the three-way control valve 3. In this design, heating is performed through the carbon tube 51 so as to provide a high temperature condition, and then the $SiO_2$ in the coal dust is convenient to react with the heated carbon tube 51.

In one embodiment, a first insulation layer 53 is disposed outside the air inlet heating tape 52, and the first insulation layer 53 includes an air inlet high temperature resistant quartz felt 531, an air inlet high temperature resistant quartz fiber 532 and an air inlet high temperature resistant insulation cotton 533 from inside to outside. In this design, an insulation effect may be provided to the $SiO_2$ reaction tube 5, so as to ensure the reaction temperature and to avoid the resource waste.

In one embodiment, the photoacoustic spectrometry detection device 4 includes a photoacoustic cavity 41 communicated with the connecting pipeline 31, a laser device 42, a signal modulator 43, a reflector 44, quartz windows 45 disposed at two ends of the photoacoustic cavity 41, a rheomicrophone 46 disposed at a middle of the photoacoustic cavity 41, a lock-in amplifier 47 for collecting and amplifying a photoaccoustic signal generated by the rheomicrophone 46 and a detection software 48; and the laser device 42 outputs laser through the signal modulator 43, and after the reflector 44 reflects the laser, the laser enters the photoacoustic cavity 41 through the quartz windows 45. In this design, after the coal dust enters the photoacoustic cavity 41 and the laser device 42 outputs the laser through the signal modulator 43, the reflector 44 reflects the laser and then the laser enters the photoacoustic cavity 41 through the quartz windows 45. The CO gas is stimulated based on the photoacoustic effect, so as to generate a sound pressure wave section, and then the rheomicrophone 46 disposed on the photoacoustic cavity 41 is driven to generate the photoacoustic signal. After the photoacoustic signal is collected and amplified by the detection lock-in amplifier 47 modulated through the modulation signal, the detection CO content may be displayed on the detection software 48.

In one embodiment, the photoacoustic spectrometry detection device further includes a sampling pump 49 for extracting gas and a flowmeter 50 disposed on the sampling pump 49. In this design, the sampling pump 49 is disposed so as to provide power for extracting the coal dust, and the coal dust may enter inside the photoacoustic cavity 41; and the flow entering the coal dust may be controlled by providing the flowmeter 50.

In one embodiment, the system further includes a tail gas treatment device 6, which includes a tail gas conversion tube 61 communicated with an air outlet of the sampling pump 49 and a NaOH liquid bottle 62 communicated with the tail gas conversion tube 61, and the NaOH liquid bottle 62 is provided with an air outlet tube 63 for discharging the processed tail gas. In this design, the tail gas treatment device 6 is disposed, so that the detected gas is subjected to tail gas treatment conveniently. Since the detected gas carries CO, the environment pollution caused by the direct discharge of the carried CO gas is avoided.

In one embodiment, the tail gas conversion tube 61 includes an oxidized copper tube 611 and an air outlet heating tape 612 for heating the oxidized copper tube 611 from inside to outside. In this design, the oxidized copper tube 611 is disposed and heated through the air outlet heating tape 612, so that the CO in the detected gas is convenient to react.

In one embodiment, a second insulation layer 613 is disposed outside the air outlet heating tape 612, and the second insulation layer 613 includes an air outlet high temperature resistant quartz felt 601, an air outlet high temperature resistant quartz fiber 602 and an air outlet high temperature resistant insulation cotton 603 from inside to outside. In this design, an insulation effect may be provided to the tail gas conversion tube 61, so as to perform the reaction conveniently and to avoid the resource waste.

In one embodiment, the temperature probes 54 are respectively disposed on the $SiO_2$ reaction tube 5 and the tail gas conversion tube 61. In this design, the temperature probes 54 are disposed, so that the temperatures of the $SiO_2$ reaction tube 5 and the tail gas conversion tube 61 are conveniently controlled, so as to perform the reaction conveniently.

Preferably, a first filtering membrane 11 is disposed on the first sampling tube 1. In this design, the coal dust entering through the first sampling tube 1 may be filtered, so as to intercept solid particles in the coal dust.

Preferably, a second filtering membrane 32 is disposed on the connecting pipeline 31. In this design, the coal dust entering the photoacoustic cavity 41 may be filtered, so as to intercept the solid particles in the coal dust.

A method for detecting a concentration of free $SiO_2$ in coal dust adopts the above system for detecting the concentration of the free $SiO_2$ in the coal dust, and the detection steps are as follows:

Step 1: regulating a three-way control valve 3 to a background sampling gas circuit, namely, a gas circuit of a first sampling tube, and at this time, an object to be measured entering a photoacoustic spectrometry detection device 4 being background CO of the coal dust;

Step 2: starting a sampling pump 49 for air exhaust, controlling coal dust entering flow through a flowmeter 50, the coal dust entering through the first sampling tube 1; and after filtering dust particles in the coal dust under an action of the first filtering membrane 11, the coal dust entering the photoacoustic cavity 41 through the three-way control valve 3 and after being filtered by the second filtering membrane 32 again;

Step 3: a laser device 42 outputting a square wave modulation signal through a signal modulator 43 to send out 2.3 μm mid-infrared laser, measuring CO gas based on 2.3 μm mid-infrared tunable diode laser 42, selecting a CO absorption line at 4300.699 cm-1 as a sensing target, a reflector 44 reflecting the laser and then the laser entering the photoacoustic cavity 41 through quartz windows 45, the laser stimulating the CO gas based on the photoacoustic effect so as to generate a sound pressure wave section and drive a rheomicrophone 46 disposed on the photoacoustic cavity 41 to generate a photoacoustic signal, and the photoacoustic signal being in direct proportion to the background CO content $Sco_{background}$;

Step 4: a detection lock-in amplifier 47 modulated by a signal modulator 43 collecting and amplifying the photoacoustic signal generated by the rheomicrophone 46, and displaying the background CO content $Sco_{background}$ on a detection software 48;

Step 5: regulating the three-way control valve 3 to a gas circuit of a second sampling tube 2, the coal dust to be detected entering a $SiO_2$ reaction tube 5 through the second sampling tube 2, an air inlet heating tape 52 heating a carbon tube 51, arranging an air inlet high temperature resistant insulation cotton 533, an air inlet high temperature resistant quartz fiber 532 and an air inlet high temperature resistant quartz felt 531 outside the carbon tube 51 for insulation, and temperature probes 54 controlling a temperature of the $SiO_2$ reaction tube 5 as 300-500 DEG C.;

Step 6: at 300-500 DEG C., based on the formula 1, a gaseous free SiO₂ in the coal dust reacting and generating solid Si and gaseous CO, after filtering the dust particles in the gas through the three-way control valve 3 under the action of the second filtering membrane 32, the reacted gas entering the photoacoustic cavity 41, repeating the step 3 to detect the gas, at this time, obtaining the reacted total CO content $Sco_{total}$, subtracting the background CO content $Sco_{background}$ to obtain $Sco_{reaction}$ generated by the gaseous free SiO₂ reaction, and then obtaining the gaseous free SiO₂ content according to the formula 1;

$$SiO_2+2C=\text{high temperature}=Si+2CO \quad \text{(formula 1)}$$

Step 7: a sampling pump 49 delivering detected tail gas to a tail gas treatment device 6, the air inlet heating tape 52 heating an oxidized copper tube 611, arranging the air inlet high temperature resistant insulation cotton 533, the air inlet high temperature resistant quartz fiber 532 and the air inlet high temperature resistant quartz felt 531 outside the oxidized copper tube 611 for insulation, the temperature probes 54 controlling the temperature of the oxidized copper tube 611 as 300-500 DEG C., and at a high temperature and based on the formula 2, CuO in the oxidized copper tube 611 reacting with CO in the tail gas to generate solid Cu and gaseous CO₂;

$$CO+CuO=\text{high temperature}=Cu+CO_2 \quad \text{(formula 2)}$$

Step 8: after reaction in step 7, the tail gas with CO₂ entering a NaOH liquid bottle 62, based on the formula 3, CO₂ reacting with the liquid NaOH to generate liquid NaCO₃ and H₂O, which are discharged through an air outlet tube 63 after completing the tail gas treatment.

$$2NaOH+CO_2=Na_2CO_3+H_2O \quad \text{(formula 3)}$$

Specifically, after being equipped with a safety shell, the system provided by the present disclosure may be applied in various complicated environments of mines, and the detection precision is not affected by the environment.

The present disclosure is not apparently limited to the details of the above exemplary embodiments for those skilled in the art, and those skilled in the art may implement the present disclosure in other specific forms without departing from the spirit and basic features of the present disclosure. Therefore, in any case, the embodiment should be regarded as the exemplary embodiment, rather than the restrictive embodiment. The scope of the present disclosure is limited by the appended claims instead of the above description. Therefore, all changes in the meaning and scope of the equal conditions of the claims shall be included in the present disclosure.

What is claimed is:

1. A system for detecting a concentration of free SiO₂ in coal dust, comprising a first sampling tube and a second sampling tube for sampling the coal dust, a three-way control valve communicated with the first sampling tube and the second sampling tube respectively, a photoacoustic spectrometry detection device communicated with the three-way control valve through a connecting pipeline, and a SiO₂ reaction tube for reacting SiO₂ in the coal dust; and the SiO₂ reaction tube is disposed on the second sampling tube;

wherein the SiO₂ reaction tube comprises a carbon tube and an air inlet heating tape from inside to outside, the carbon tube is heated through the air inlet heating tape, the SiO₂ in the coal dust delivered by the second sampling tube reacts with the heated carbon tube, and reacted gas is delivered into the photoacoustic spectrometry detection device through the three-way control valve;

the photoacoustic spectrometry detection device comprises a photoacoustic cavity communicated with the connecting pipeline, a laser device, a signal modulator, a reflector, quartz windows disposed at two ends of the photoacoustic cavity, a rheomicrophone disposed at a middle of the photoacoustic cavity, a lock-in amplifier for collecting and amplifying a photoaccoustic signal generated by the rheomicrophone and a detection software; and the laser device outputs laser through the signal modulator, and after the reflector reflects the laser, the laser enters the photoacoustic cavity through the quartz windows;

the photoacoustic spectrometry detection device further comprises a sampling pump for extracting gas and a flowmeter disposed on the sampling pump;

the system further comprises a tail gas treatment device, which comprises a tail gas conversion tube communicated with an air outlet of the sampling pump and a NaOH liquid bottle communicated with the tail gas conversion tube, and the NaOH liquid bottle is provided with an air outlet tube for discharging the processed tail gas.

2. The system for detecting the concentration of the free SiO₂ in the coal dust according to claim 1, wherein a first insulation layer is disposed outside the air inlet heating tape, and the first insulation layer comprises an air inlet high temperature resistant quartz felt, an air inlet high temperature resistant quartz fiber and an air inlet high temperature resistant insulation cotton from inside to outside.

3. The system for detecting the concentration of the free SiO₂ in the coal dust according to claim 1, wherein the tail gas conversion tube comprises an oxidized copper tube and an air outlet heating tape for heating the oxidized copper tube from inside to outside.

4. The system for detecting the concentration of the free SiO₂ in the coal dust according to claim 3, wherein a second insulation layer is disposed outside the air outlet heating tape, and the second insulation layer comprises an air outlet high temperature resistant quartz felt, an air outlet high temperature resistant quartz fiber and an air outlet high temperature resistant insulation cotton from inside to outside.

5. The system for detecting the concentration of the free SiO₂ in the coal dust according to claim 1, wherein temperature probes are respectively disposed on the SiO₂ reaction tube and the tail gas conversion tube.

* * * * *